United States Patent [19]

St. Martin

[11] Patent Number: 5,318,902

[45] Date of Patent: * Jun. 7, 1994

[54] BIPHASIC CRYSTALLINE SEPARATION OF WATER INSOLUBLE ORANGE PIGMENTS FROM MONASCUS SPECIES

[75] Inventor: Edward J. St. Martin, Libertyville, Ill.

[73] Assignee: UOP, Des Plaines, Ill.

[ * ] Notice: The portion of the term of this patent subsequent to May 22, 2007 has been disclaimed.

[21] Appl. No.: 948,040

[22] Filed: Sep. 21, 1992

Related U.S. Application Data

[63] Continuation-in-part of Ser. No. 547,704, Jul. 3, 1990, abandoned, which is a continuation-in-part of Ser. No. 261,805, Oct. 24, 1988, abandoned.

[51] Int. Cl.$^5$ .................... C12P 17/00; C12N 1/14
[52] U.S. Cl. .................... 435/117; 435/118; 435/119; 435/134; 435/911; 435/256.8
[58] Field of Search ............... 435/119, 117, 134, 118, 435/911, 254, 256.8

[56] References Cited

U.S. PATENT DOCUMENTS

| | | | |
|---|---|---|---|
| 4,145,254 | 3/1979 | Shepherd et al. | 195/81 |
| 4,442,209 | 4/1984 | Miyake et al. | 435/119 |
| 4,927,760 | 5/1990 | St. Martin | 435/191 |

OTHER PUBLICATIONS

Aouo et al., *Agric. Biol. Chem.*, vol. 55 (7) pp. 1935-1938, 1991.
Inoue et al., *Nature*, vol. 338, pp. 264-266, 1989.
The Merck Index, pp. 972-978, 1983.
Lin, *J. Ferment. Technol.*, 51, 407 (1973).
Hawksworth and Pitt, *Aust. J. Bot.*, 31, 51 (1983).
*Food Technology*, p. 49 (Jul., 1986).
B. C. Fielding et al., Tetrahedron Letters No. 5, 24-7 (1960).
Kumasaki et al., *Tetrahedron*, 18, 1171 (1962).
Rehm et al. "Biotechnology", vol. 2, 1985, pp. 294-309.

*Primary Examiner*—Irene Marx
*Attorney, Agent, or Firm*—Thomas K. McBride; Eugene I. Snyder

[57] ABSTRACT

Several classes of water immiscible lipophilic phases effect the transfer of crystalline orange precursor pigments produced by Monascus species in an aqueous culture medium from the aqueous to the lipophilic phase without solubilizing a major portion of the pigment. Liquid vegetable and mineral oils are two such classes. This phenomenon permits high recovery of pigment in a simple and convenient manner, and also permits development of a batch recycle and a continuous fermentation process for pigment production.

17 Claims, 1 Drawing Sheet

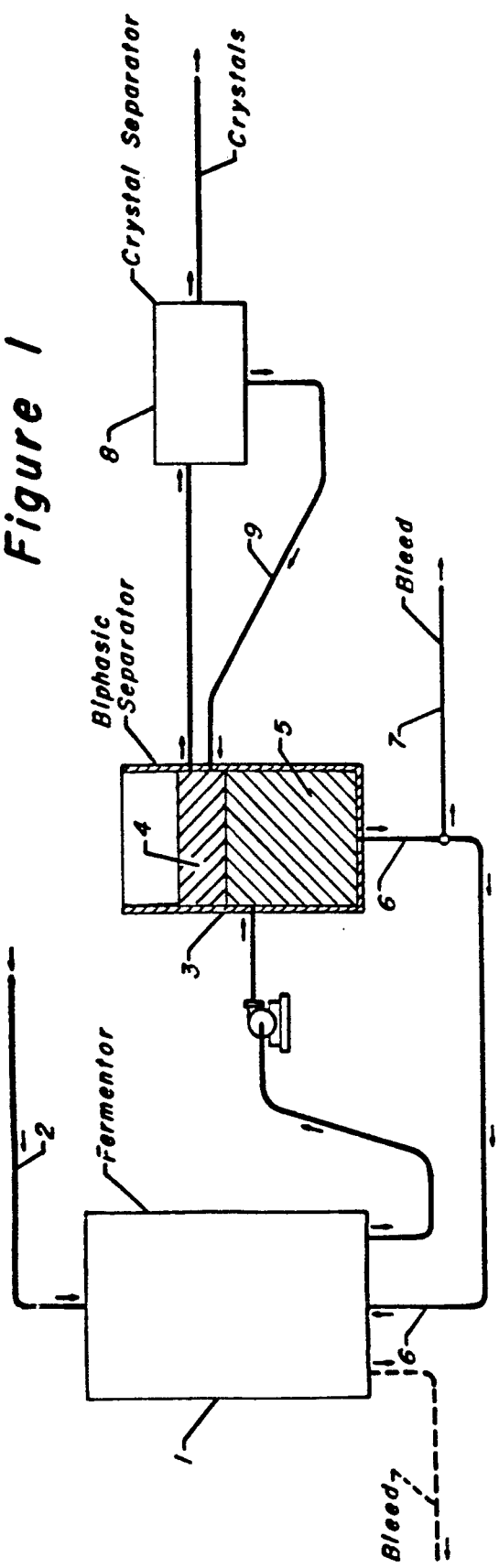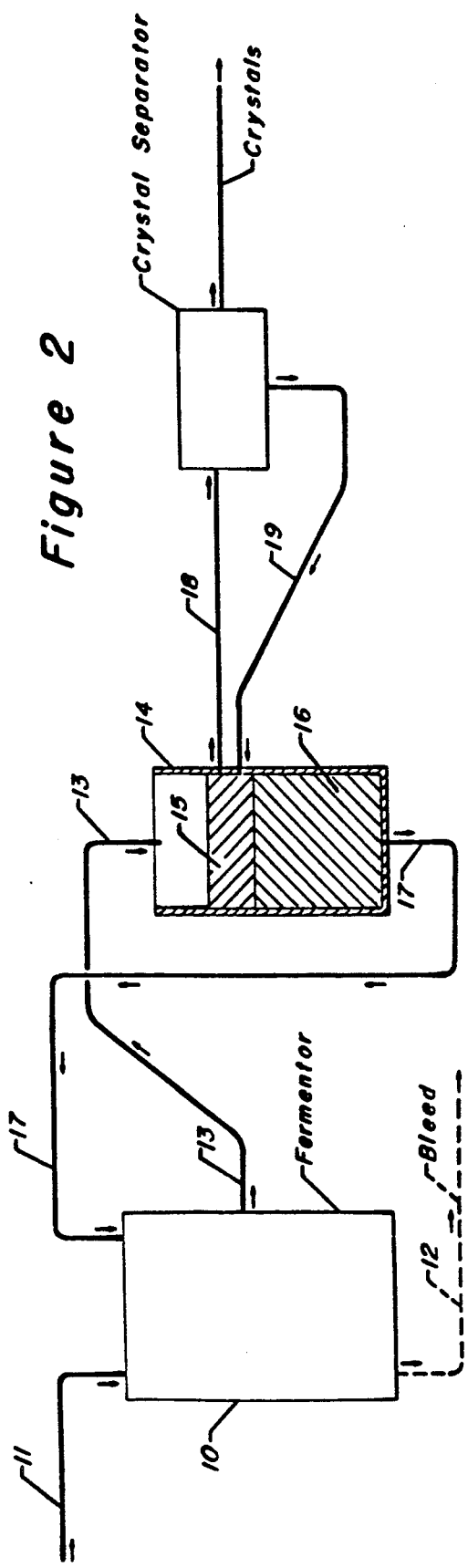

BIPHASIC CRYSTALLINE SEPARATION OF WATER INSOLUBLE ORANGE PIGMENTS FROM MONASCUS SPECIES

CROSS REFERENCE TO RELATED APPLICATION

This application is a continuation-in-part of my copending application, Ser. No. 547,704 filed Jul. 3, 1990, now abandoned, which is a continuation-in-part of Ser. No. 261,805, filed Oct. 24, 1988, now abandoned, all of which is hereby incorporated by reference.

BACKGROUND OF THE INVENTION

"We live in a world of color—color is in the trees and sky around us, in our clothes, and in our homes. When the colors of familiar things differ from what we expect, we are usually upset—greenish skies warrant of bad weather, black clothes denote mourning, intense colors in the home stimulate or agitate. The same applies to food. Consumers first judge the quality of the food product by its color." Food Technology, page 49 (July, 1986). However much one may decry a consumer attitude which places higher priority on visual impact than on gustatory and nutritional value, it is an attitude which must be actively confronted in the marketplace.

Although naturally occurring pigments perforce were the first used food colorants, the development of chemistry as a discipline led to many synthetic dyes, especially anilines, to supplant naturally occurring pigments as food additives. As a class synthetic colorants have many advantages, such as a uniform and reproducible color, color stability, absence of flavor, and an oxidative and/or thermal and/or photostability superior to naturally occurring pigments, broad availability relatively insensitive to changes in crop yields and so forth. As a result, the popularity of synthetic colorants at least is understandable.

However, with heightened awareness of a consuming public to food additives and increased testing of some representative examples came a concern about their safety. Recent years have seen some materials formerly used as food colorants run the gamut from being beyond reproach to being suspect and even banned or at least used restrictedly. For example, FD&C Red No. 2 and FD&C Violet No. 1 have been banned in the United States and many other countries. Because of a variety of allergic reactions in sensitive individuals induced by FD&C Yellow No. 5 a recent ruling by the FDA requires food colored with it be declared as such on product labels. As a consequence the pendulum has begun to swing once more toward naturally occurring pigments as food additives.

The pigments produced by Monascus species traditionally grown on rice in the Orient are orange and relatively insoluble in water, but readily react with compounds containing amino groups to form water soluble red colorants. The water-insoluble orange pigments elaborated by Monascus have been used in the Orient for hundreds of years as a general food colorant and as a colorant for wine and bean curd, can be made water soluble or oil soluble, are stable at a pH range 2-10, are heat stable and can be autoclaved. In oriental countries Monascus microorganisms typically are grown on grains of rice and once the grains have been penetrated by the orange-red mycelium the whole mass is finely ground with the resulting powder used as a food colorant. The orange pigment is a mixture of monascorubrin and rubropunctatin, whose structures were elucidated by B. C. Fielding et al., Tetrahedron Letters No. 5, 24-7 (1960) and Kumasaki et al., Tetrahedron, 18, 1171 (1962), and which differ in the former having a 7-carbon ketonic group and the latter having a 5-carbon ketonic group. For the purposes of this application, "precursor pigment" refers to any mixture of water insoluble orange pigment containing monascorubrin and rubropunctatin as produced by fermentation of a suitable Monascus species.

Commercial production of precursor pigment requires development of a suitable fermentation procedure, which has been the subject of many reports in recent years. Shepherd et al., U.S. Pat. No. 4,145,254, made an important advance by using a two-stage process in which the microorganism first was cultivated at pH 4-7 in a growth-promoting medium, then was transferred to a second medium at pH 2-4 to stimulate precursor pigment production. The low pH did not interfere with precursor pigment production but inhibited its subsequent reaction with amino groups of proteins and/or ammonium ions in the medium. The result was the exclusive production of orange precursor pigment as a colorant. As another example U.S. Pat. No. 4,442,209 claims to increase precursor pigment formation by cultivating a Monascus species in a medium containing maltitol.

As Shepherd et al. noted, ". . . if it is desired commercially to obtain a pigment having a perfectly determined structure which may be subjected to rigorous tolerance tests and which shows perfectly reproducible properties, it is the high-yield production of a high-purity orange pigment which should be researched in the first instance." All processes described to data retain serious disadvantages associated with the separation and isolation of high purity precursor pigment. The shortcomings and difficulties inherent in the recovery of precursor pigment using prior art methods of precursor pigment production, as well as the stark contrast between our method of pigment production as embodied in the claimed invention and the prior art approach, will become apparent by a short sojourn through the prior art.

During fermentation of Monascus species the precursor pigment is produced as a metabolite strongly associated with lipids produced by the fungus. The precursor pigment is not elaborated extracellularly but remains in the mycelium as a lipid complex. Although some of the precursor pigment can be isolated by extracting the entire concentrated culture (cells plus broth) with a solvent such as ethanol at room temperature, more complete precursor pigment recovery requires that the fungal cell membranes and lipids be dissolved to release the associated precursor pigment. The majority of the pigment can only be released from the fungal cell mass by repeated extraction with hot solvents such as methanol, ethanol, isopropyl alcohol, ethyl ether or chloroform in a reflux apparatus.

Cell membrane lysis with hot solvents affords the precursor pigment-lipid complex as an ill-defined heterogeneous dispersion of liquid fatty globules. Because the fatty liquid can not be directly separated from the aqueous phase in which it is dispersed, typically one extracts the mixture with a water-insoluble organic solvent to afford as an extract a solution of the precursor pigment-lipid complex plus a myriad of other organic lipophilic components released upon cell lysis. Removal of solvent from the extract affords as a concentrate organic material generally containing substantially less than 50 percent precursor pigment, a direct consequence of strong pigment-lipid association. Crystallization of the precursor pigment from the concentrate using a suitable organic solvent then can afford, for the first time, crystalline precursor pigment of perhaps 90 percent purity, with subsequent recrystallization necessary to achieve higher purity. In other variants the precursor pigment is separated from lipids and purified by chromatography.

The foregoing extraction-chromatography-crystallization procedures are inefficient as regards yield of the purified precursor pigment. The procedures also are costly because of the use of solvents to extract the pigment and the necessity of expending energy to evaporate solvent from the extract. Such procedures also are not readily adaptable to continuous fermentation with continuous precursor pigment production.

Although there may be other aspects of precursor pigment production from Monascus which need attention, for example, obtaining suitable mutants or otherwise genetically altered microorganisms, this application is directed solely to an improvement in precursor pigment production which eliminates the need for costly extraction methods. My invention is based on several interrelated observations which serve as gross departures from the prior art. One critical observation is that in the fermentation of Monascus species the orange precursor pigment can be induced to form as a crystalline, extracellular product. The second observation is that crystalline, extracellular orange precursor pigment as formed in fermentation of Monascus species migrates to a lipophilic phase in contact with the culture medium. Especially where the lipophilic phase is chosen as to only slightly solubilize the crystalline pigment, the resultant aggregation of crystalline pigments in a water immiscible oil phase permits their facile separation merely by separating the lipophilic phase from the aqueous phase and collecting the crystals dispersed in the former. Of enormous significance is the fact that the collected crystals, after removal of adhering lipophilic phase, may be as high as 99% pure! My discovery also permits the development of both a batch recycle process for crystalline pigment production as well as a process based on continuous fermentation. In my process no toxic solvents are used which kill the cells, and the latter can be used for repeated cycles of pigment production.

SUMMARY OF THE INVENTION

This invention has as its goal that of effecting an inexpensive, simple, and convenient separation and recovery of the water-insoluble orange pigments produced by Monascus species. An embodiment comprises growing Monascus species in a culture medium under conditions affording pigment as a water-insoluble crystalline product in the culture medium, contacting the medium with a water immiscible lipophilic phase in which the crystalline pigment has only limited solubility, and collecting the crystalline pigment congregating as a solid in the lipophilic phase. In a more specific embodiment the lipophilic phase is a liquid vegetable oil. In a still more specific embodiment the lipophilic phase is corn oil or soybean oil at a concentration from 1 to about 10 weight percent. In still another specific embodiment the lipophilic phase is mineral oil. Other embodiments will be apparent from the ensuing discussion.

DESCRIPTION OF THE FIGURES

FIG. 1 is a schematic representation of a batch recycle process for production of orange precursor pigment.

FIG. 2 is a schematic representation of a continuous fermentation process with production of orange precursor pigment.

DESCRIPTION OF THE INVENTION

I have discovered that when a water immiscible lipophilic phase which only sparingly dissolves precursor pigment is added to a Monascus species culture medium containing crystalline precursor pigment, the crystals migrate from the aqueous phase to the lipophilic phase without accompanying dissolution. The presence of crystalline pigment in the lipophilic phase allows its facile separation, as by centrifugation or filtration of the separated lipophilic phase, to afford rather pure crystalline pigment. Where the solubility of the pigment in the lipophilic phase is low its percentage recovery is high. Since the lipophilic phase after crystal removal can be reused even where the pigment is appreciably soluble in the lipophilic phase, the latter quickly becomes saturated with pigment and subsequent to its saturation the percentage recovery of pigment is high. My observation permits not only a simple, inexpensive, and convenient separation of the precursor pigment from Monascus species, but also permits both a batch recycle process for precursor pigment production and a process for precursor pigment production using continuous fermentation of Monascus species.

As previously stated, Monascus species have long been known to make as a metabolite a water insoluble orange pigment as a mixture of monascorubrin and rubropunctatin, which we refer to in this application as precursor pigment. There may be used in the practice of my invention any Monascus species which produces precursor pigment in an amount sufficient to exceed its solubility limits in the pigment producing culture medium. For all practical purposes, this requirement translates to formation of at least 30 milligrams per liter of precursor pigment at pigment producing conditions. Suitable Monascus species are readily obtainable from various sources. For example, Lin [J. Ferment. Technol., 51, 407 (1973)] has described numerous isolates from Koji (sediment) of Koaliang brandy. Similar isolates can be easily obtained from other oriental fermented foods colored with the Monascus mold, such as red rice, red rice wine and red soybean cheese. Lin also has reported numerous species publicly available as type cultures from several sources. In their taxonomic study Hawksworth and Pitt [Aust. J. Bot., 31, 51 (1983)] examined a multitude of isolates, many of which were publicly available from depositories or readily isolated from oriental fermented food.

From the foregoing it needs to be noted that suitable strains of Monascus species occur widely, that many are available from depositories, and that still more can be routinely isolated from oriental fermented food. Thus, subject to the requirement of a rather modest level of precursor pigment production the Monascus strains used in the practice of our invention are merely a matter of choice with a very large number of strains readily available to anyone. Although such species as *M. purpureus, M. major, M. rubiginosus* and *M. anka* have been cited as precursor pigment producers, the taxonomic work of Hawksworth and Pitt suggests these may need to be reclassified.

A suitable Monascus species is grown in an aqueous pigment producing culture medium containing at least one agent which induces crystalline pigment formation. Suitable agents and their use have been described in U.S. Pat. No. 4,927,760, all of which is incorporated by reference. Such crystalline pigment inducers are of various types, one of which is poly(oxyethylene)sorbitan esters, which commonly are known under the trademark of TWEEN. In particular, TWEEN 20, TWEEN 40, and TWEEN 80 have been found to be particularly effective not only in inducing crystalline pigment formation, but also in producing large crystals. All the aforementioned TWEENS are a mixture of esters whose fatty acid component includes palmitic acid. The TWEENS may be effective at a concentration as low as about 0.01 weight percent, but it is recommended that they be used at a concentration of at least about 0.1 and as high as about 1 weight percent in the culture medium.

Another class of crystal inducers consists of liquid vegetable oils, especially corn oil and soybean oil, but also including such materials as cottonseed, peanut, sunflower, safflower, sesame, rapeseed and olive oils and the liquid portion of palm oil. When vegetable oils are used as crystalline pigment inducers they are employed in an amount between 0.1 and about 10 weight percent of the culture medium. A third class of crystalline pigment inducers consists of certain glycerol triesters, especially triolein, tripalmitolein, tripetroselinin, and any combination of them.

The crystalline orange precursor pigments formed in the presence of the aforementioned inducers are quite lipophilic. When a water immiscible lipophilic phase is added to the culture medium containing water-insoluble crystalline pigment, crystals migrate as a solid phase from the aqueous to the lipophilic phase and become concentrated there. Although the nature of the lipophilic phase is not very important with respect to the property of crystal migration alone, it is important when used in the process of this invention. In particular, it is very important to the success of this invention that the lipophilic phase be biocompatible. By "biocompatible" is meant that both cell growth and cell metabolism are unaffected. That is, biocompatible lipophilic phases are oils which do not interfere with cell growth and do not substantially affect cell metabolism. For Monascus species in particular liquid vegetable oils form one class of biocompatible lipophilic phase important in the practice of this invention. Another such class are higher alkanes, i.e., alkanes having at least 14 carbon atoms. The class of liquid vegetable oils used in my invention include corn, soybean, sesame, peanut, safflower, sunflower, rapeseed, and olive oils.

Liquid vegetable oils have the property of also being crystalline pigment inducers; vide supra. Consequently, when liquid vegetable oils are used as the lipophilic phase in the practice of this invention no other material needs to be added to the fermentation broth to induce crystal formation. Disadvantages arise from the use of liquid vegetable oils in the practice of this invention owing to their slow hydrolysis upon contact with the aqueous culture medium and their tendency to form emulsions upon being contacted with the medium, although neither disadvantage is sufficiently serious to preclude the use of liquid vegetable oils as a class in the practice of my invention.

Neither of the foregoing disadvantages are manifested by the mineral oils which, for this reason as well as others, are even more highly recommended in the practice of this invention. Mineral oils are mixtures of saturated paraffins (alkanes) and cycloparaffins (cycloalkanes) produced by the petroleum industry and come in grades—heavy and light mineral oil—differing in viscosity and boiling point which reflect their composition as a mixture of alkanes and cycloalkanes. However, the compositional range of available mineral oils is quite limited, with the mineral oils consisting of $C_{15}$–$C_{20}$ aliphatic hydrocarbons. See Kirk-Othmer, "Encyclopedia of Chemical Technology", 3rd Ed., V. 11, pp. 704–5 (1980); "Merck Index", 11th Ed., p. 1139, item 7139 (1989); U.S. Pharmacopaeia, XX11, pp. 899–900. Of course, alkanes, cycloalkanes, and their mixtures also may be used in the practice of this invention provided they have at least 14 carbon atoms when used per se to ensure biocompatibility.

Because mineral oils and biocompatible alkanes and cycloalkanes do not induce crystal formation, they must be used as the lipophilic phase only in conjunction with other agents which induce crystalline pigment formation. In this connection mixtures of mineral and vegetable oils are a highly favored lipophilic phase, incorporating advantages of both kinds of oils in a synergistic manner, and mixtures containing from 2 to about 30 weight percent vegetable oil, even more preferably from about 5 to about 20 weight percent vegetable oil, are highly recommended. With the aforementioned mixtures the hydrolytic tendencies and emulsion-forming properties of the vegetable oils are minimized, the solubility of the precursor pigment in the lipophilic phase remains low, (vide infra), and no added crystalline pigment inducers are required.

In practice it is desirable to have as little lipophilic phase as possible for ease of handling, for minimizing cost, and for minimizing any loss arising from solubilized pigment therein. However, enough lipophilic phase is needed in order to have separate phases and to afford sufficient capacity for concentrating all the pigment crystals present in the culture medium. Although as little as about 0.5 weight percent lipophilic phase may be used, with the upper limit usually not exceeding 20 weight percent, the range between about 1 and about 10 weight percent, based on culture medium, appears to be most convenient. However, amounts of oil in excess of 20 weight percent may be used in appropriate cases, such as the continuous process described below, without apparent detriment.

The solubility of the pigment in the lipophilic phase is an important factor only in the sense of its representing an initial loss of pigment (since only the crystalline pigment is collected), but it is unimportant in the overall practice of this invention since the lipophilic phase may be reused and will be saturated with respect to pigment after its first use. Stated differently, once the lipophilic phase becomes saturated with precursor pigment it becomes an ideal phase in that the incremental solubility of precursor pigment in the saturated lipophilic phase is zero; no more pigment dissolves. Consequently, the only pigment loss arises from the first use of the lipophilic phase. The orange precursor pigment should have a solubility in the lipophilic phase of no more than 50 g/liter, desirably no more than about 10 g/liter, even more desirably less than about 5 g/liter, and most preferably no more than about 1 g/liter. The class of mineral oils and biocompatible alkanes and cycloalkanes are especially recommended lipophilic phases in the practice of this invention because of the low solubility of the pigment therein. Although the solubility of the pigment is somewhat higher in the members of the class of liquid vegetable oils, the latter perform quite satisfactorily in the practice of my invention. It may be mentioned in passing that the solubility of the pigment in the various liquid vegetable oils can be expected to be quite similar, reflecting the fact that the members all are triglycerides of fatty acids almost exclusively in the $C_{14}$–$C_{22}$ range. For reasons explicated more fully above, mixtures of mineral and vegetable oils are particularly preferred.

The culture medium containing crystalline pigments is contacted with the lipophilic phase for a time sufficient to effect transfer of crystalline pigment from the aqueous culture medium to the lipophilic phase. When such transfer is complete the lipophilic and aqueous phases are separated. The insoluble crystalline pigments which are concentrated in and dispersed through the lipophilic phase are then recovered, as by filtration or centrifugation. The precise means of recovery will be readily recognized by one skilled in the art, since it is no more than a classical separation of solid dispersed in a liquid medium, and will not be further discussed.

It is possible to incorporate the previously described invention into several efficient processes for the production of orange precursor pigment, two of which are shown in the figures. FIG. 1 schematically represents one such process which we refer to as a batch recycle process. FIG. 2 is a schematic representation of another process utilizing continuous fermentation for the production of precursor pigment from Monascus species. Both will be described in somewhat greater detail below, but it needs to be emphasized that these processes are only illustrative of those incorporating our invention and do not exhaust the multiplicity of variants which may be successfully employed.

In FIG. 1 a fermentation unit, 1, contains cells, pigment producing culture medium, and crystal inducers. Fresh nutrients are added as necessary at 2 and the tank is equipped with a stirrer, provisions for aeration, and so forth, as is typical for a fermentor. There is an optional bleed on the fermentor to prevent overflow or overfill as fresh nutrients are added. After fermentation has proceeded for a time sufficient to produce a mass of crystalline orange precursor pigments, which usually is a period between about 2 and about 30 days, the contents of the fermentation unit, or some portion thereof, is transferred to a phase separator, 3, either containing, or to which is added, a lipophilic phase, 4. The lipophilic phase and aqueous culture medium, 5, are contracted for a time sufficient to effect transfer of the crystals from the aqueous to the lipophilic phase, which usually requires some mixing of the two phases. At a time when it is judged that crystal migration to the lipophilic phase is complete, mixing is stopped and the phases are allowed to separate. The aqueous phase, which consists of cells plus depleted culture medium, is then recycled to the fermentation unit via recycle stream, 6, with an optional bleed, 7, incorporated to prevent overfill as concentrated fresh nutrients are added to replenish the culture medium. The lipophilic (oil) phase from the phase separator is transferred to a crystal separator, 8, where the crystals are separated from the lipophilic phase and the lipophilic phase returned to the phase separator through line 9. The crystal separator may be merely a filtration unit or a centrifuge.

It has been found that the precursor pigment so formed is rather pure except for oil which may adhere to the crystals. Where it is desirable to remove this oil and other material adsorbed by the crystals, the crystals may be washed with a low boiling organic solvent in which the precursor pigment is relatively insoluble. Thus, hexane is a quite desirable washing medium, and ethanol or methanol also can be used. Simply washing the crystals to remove adhering and entrapped lipophilic phase may afford crystalline precursor pigment with a purity in the 95–99 percent range. For still further purification the pigments may be recrystallized, as from methanol, ethanol or isopropyl alcohol. However, since the precursor pigment generally is used as a raw material in further production of water soluble pigments subsequent processing is generally unnecessary. It also should be explicitly recognized that variants of the foregoing process include the use of vegetable oils as crystal inducers, which necessarily affords a two-phase system in the fermentation unit. Another variant includes the use of a vegetable oil-mineral oil mixture as both crystal inducer and lipophilic phase, in which case the lipophilic phase is already present in the fermentation unit and need not be added to the phase separator.

FIG. 2 represents a variant in which crystalline pigment is produced in a continuous fermentation process. Thus, the continuous fermentation unit, 10, contains cells of a suitable Monascus species, pigment producing culture medium, and crystal inducers. Concentrated nutrients are added at 11 as they are depleted, and a bleed, 12, in the fermentation unit provides for a set of steady state conditions. A portion of the culture medium from the continuous fermentation unit is continuously transferred through line 13 to a biphasic separator, 14, where the aqueous culture medium containing the crystalline precursor pigment is caused to pass through a column of a lipophilic phase, 15. As the aqueous phase passes through the oil the crystals are transferred and concentrate in the oil phase. Since only a portion, usually a small fraction, of the culture medium is contacted with the lipophilic phase at any time, this variant has the advantage that a smaller total amount of oil phase may be utilized relative to the batch-recycle method. However, the amount of the lipophilic phase may remain unchanged to afford a relatively high ratio of oil to aqueous phases in the biphasic separator. The aqueous culture medium, 16, in the biphasic separator which is stripped of crystalline pigment is then returned via 17 to the continuous fermentor. As crystals mass in the lipophilic phase of the biphasic separator, a portion of the lipophilic phase is periodically withdrawn at 18 and transferred to a crystal separator, as described above. The clarified lipophilic phase is returned at 19 to the biphasic separator, and the separated crystals are recovered and, where necessary, washed and.or recrystallized as described above.

As with the batch process, many variants are possible, including the use of vegetable oils as crystal inducers and mixtures of vegetable and mineral oils as both the lipophilic phase and crystal inducer. The use of a vegetable-mineral oil mixture as the lipophilic phase in the fermentation unit may be particularly advantageous, since the system behaves as if precursor pigment crystallized directly in the lipophilic phase.

Further variants on each of the above schemes will be apparent to the skilled worker and are intended to be encompassed by our basic invention. The examples below illustrate our invention, but are only representative thereof. The examples in no way are intended to limit or circumscribe my invention to what is there described.

EXAMPLE I

Typical Fermentation of Monascus. Monascus fungus was maintained on agar slants containing (per liter of medium) yeast extract (3 grams), malt extract (3 grams), bacto peptone (5 grams), glucose (10 grams), and agar (15 grams). The slants were inoculated with Monascus fungus and incubated at 30° C. for two weeks. Under these conditions the fungus makes stable sexual spores that can be stored at 4° C. for months.

A slant was used to inoculate a growth medium of approximately 100 mL of broth containing (per liter) glucose (40 g), yeast extract (10 g), $KH_2PO_4$ (3 g), and 1–10 mL of TWEEN-40. The TWEEN-40 in the growth medium prevents the cells from inducing pigment synthesis and allows the fungus to grow as a dispersed mycelium. The culture is incubated at 30° C. in a 250 mL flask with shaking at 200 rpm for 1 week.

A 10% inoculum of the above broth culture is used to inoculate 1 to 20 liters of a pigment production medium which contains (per liter of medium) $KH_2PO_4$ (1 g), $MgSO_4 \cdot 7H_2O$ (0.5 g), NaCl (0.5 g), $FeSO_4 \cdot 7H_2O$ (0.1 g), $NH_4Cl$ (0.5 g), glucose (40 g), and crystalline pigment inducer where appropriate. This culture was incubated at 28° C. with aeration, generally for about 2 weeks. Under these growth conditions the fermentation drops the pH of the medium to approximately 3.0 and pigment production is induced. After the glucose in the fermentation medium is exhausted and maximal pigment has been produced the precursor pigment crystals were harvested.

EXAMPLE II

Use of a Lipophilic Phase to Concentrate Crystals. Thirteen oils (lipophilic phases) were added at a 10% concentration to a Monascus fermentation that had produced large pigment crystals. Eight oils were not able to separate the crystals from the culture medium, viz., hexanol, isobutyl alcohol, 1-butanol, 3-methyl-1-butanol, ethylacetate, 2,4-pentanedione, methylene dichloride, and chloroform. The five oils giving phase separation of crystals were corn oil, soybean oil, hexane, mineral oil, and tetradecene.

The five oils that could effect a phase separation of orange precursor pigment crystals were evaluated for the amount of crystals that were removed from the medium and solubility of the pigment in the oil phase at ambient temperature (ca 22° C.). Although corn and soybean oil separate the crystals, a significant amount of pigment is soluble in these oils. Mineral oil, hexane, and tetradecene can partition the crystals and dissolve under 1% of the pigment as compared to over 4% solubilized by the vegetable oil. Detailed data are summarized in the following Table 1. In all cases 20 mL of a culture medium containing 33.4 milligrams of total precursor pigment (i.e., as crystals, dissolved in the culture medium, and retained in the mycelium) was contacted with 2 mL of the lipophilic phase.

TABLE 1

| Characteristics of Lipophilic Phases in Crystal Separation. | | | |
| --- | --- | --- | --- |
| Oil | Pigment Remaining in Aqueous Phase[a] (mg) | Pigment in Oil Phase, Total[b] (mg) | Pigment Soluble in Oil Phase (mg) |
| Corn Oil | 9.17 | 16.61 | 7.12 |
| Soybean Oil | 7.24 | 18.25 | 7.45 |
| Mineral Oil | 6.75 | 22.82 | 0.32 |
| Hexane | 4.48 | 23.15 | 0.61 |

TABLE 1-continued

| Characteristics of Lipophilic Phases in Crystal Separation. | | | |
| --- | --- | --- | --- |
| Oil | Pigment Remaining in Aqueous Phase[a] (mg) | Pigment in Oil Phase, Total[b] (mg) | Pigment Soluble in Oil Phase (mg) |
| Tetradecene | 6.17 | 26.73 | 0.81 |

[a]Total of pigment dissolved in medium and remaining in mycelium
[b]As crystals and dissolved in oil.

EXAMPLE III

Solubility of orange precursor pigment in vegetable oils and mineral oils. The solubility of the orange precursor pigment was determined in various liquid vegetable oils and mineral oils, all of which could function as a suitable lipophilic phase to concentrate crystals arising from Monascus fermentation by effecting phase separation of orange precursor pigments; see Example II. To a mixture of 10 milligram of pigment in 10 mL of 0.001 molar HCl was added 2 mL of the individual oils. Each sample was mixed vigorously for 10 second intervals over a period of 30 minutes to allow the crystals to partition into the oil phase and out of the water phase. The samples then were centrifuged at 1,000 rpm for 10 minutes, after which the oil phase was removed by a pipette and filtered to separate the undissolved crystals from the oil. The solid that was recovered upon filtration, the filtered oil, and the recovered water phase were separately dissolved in acidified ethanol and the optical density of the resulting solution was determined at 466 nm. From the optical density, the sample size, and the dilution of each sample there was determined the amount of pigment that dissolved in the oil phase, that dissolved in the aqueous phase, and which merely migrated to the oil phase as a solid. The results of these experiments are summarized in Table 2.

TABLE 2

| Characteristics of Vegetable and Mineral Oils in Crystal Separation | | | | | |
| --- | --- | --- | --- | --- | --- |
| | | Pigment Distribution[b] | | | |
| Oil | Weight Pigment Used[a] | Dissolved in Oil | Recovered as Crystals | Dissolved in Water | Total Recovery[b] |
| Corn | 10.6 | 5.40 | 4.92 | 0.076 | 10.4 |
| Soybean | 10.0 | 4.89 | 4.65 | 0.062 | 9.6 |
| Rapeseed (Canola) | 10.3 | 4.85 | 5.42 | 0.010 | 10.6 |
| Safflower | 10.3 | 5.34 | 4.72 | 0.048 | 10.1 |
| Sunflower | 10.4 | 5.47 | 4.79 | 0.056 | 10.3 |
| Cottonseed | 10.4 | 5.50 | 4.53 | 0.011 | 10.0 |
| Light Mineral | 10.1 | 0.17 | 8.78 | 0.007 | 9.0 |
| Heavy Mineral | 10.8 | 0.15 | 9.60 | 0.006 | 9.8 |

[a]Amount in mg. of pigment started with.
[b]Amount in mg.

These data show clearly the similarity in solubility characteristics among the various members of the class of vegetable oils and between the two members of the class of mineral oils.

EXAMPLE IV

Precursor Pigment Production via Batch Recycle Biphasic Recovery. A 100 mL culture of Monascus fungus that had been grown in broth that contained glucose (40 g/l), yeast extract (10 g/l), $KH_2PO_4$ (3 g/l) and 0.1% TWEEN-40 was used to inoculate a 2 liter fermentor with 1 L of pigment production medium described in Example I. The fermentor was run at 30° C. and pH 3.0 with 250 rpm agitation and strong aeration. The fermentor was monitored for glucose utilization and total precursor pigment production. At regular intervals the pigments were harvested using 100 mL of soybean oil to partition the pigment crystals into the oil which was subsequently removed. Additional glucose and nutrients were added to the fermentor and the fermentation was continued. Six separate recycles of the cells in this fermentor were run and different methods of adding oil, harvesting products and replacing nutrients were examined. 1) The vegetable oil was added to the fermentor at the beginning of the fermentation. 2) The vegetable oil was added to the fermentor only after the pigment crystals had been produced. 3) Only the oil was removed from the fermentor using a suction device and more glucose was added to start a second production fermentation. 4) The oil and growth medium were removed from the fermentor into a second vessel where the cells were separated and returned to the fermentor with fresh complete production medium. 5) The oil and cells were removed from the fermentor and the cells were returned to the fermentor with just one gram of $KH_2PO_4$ and 40 grams of glucose in one liter of water.

TABLE 3

| DAYS ON LINE | GLUCOSE USED | TOTAL PIGMENT | % YIELD PIGMENT/GLUCOSE |
|---|---|---|---|
| 5 | 29.3 g | 0.34 g | 1.2 |
| 7 | 18.4 | 1.55 | 8.4 |
| 9 | 22.0 | 1.73 | 7.9 |
| 11 | 23.7 | 2.18 | 9.2 |
| 13 | 19.7 | 1.44 | 7.3 |
| 18 | 24.2 | 1.65 | 6.8 |

EXAMPLE V

Precursor Pigment Production via Continuous Fermentation and Biphasic Recovery. The isolation of pigment crystals from the fermentation could be made into a continuous process by pumping the medium from the 2 liter fermentor described above through an external 500 mL separatory funnel that contained 100 mL of a vegetable oil. The fermentation medium was allowed to drop through the oil in the funnel and pigment crystals were partitioned from the medium and concentrated in the oil phase. Two cycles of continuous pigment crystal isolation were run and glucose consumption and pigment production were monitored.

TABLE 4

| DAYS ON LINE | GLUCOSE USED | TOTAL PIGMENT | % YIELD PIGMENT/GLUCOSE |
|---|---|---|---|
| 3 | 26.1 g | 0.54 g | 2.1 |
| 7 | 23.1 | 1.31 | 5.7 |

EXAMPLE VI

Precursor Pigment Purity During Production. Precursor pigments were produced during the Monascus fungus liquid fermentation as crystalline material that is suspended in a second oil phase. The lighter crystal and oil phase was removed from the more dense culture medium that contained the fungal cells by pumping the top layer into a filtration device. The crystals were removed from the bulk of the oil phase by filtration through a Whatman 451 paper filter under vacuum. The resulting crystals that still contained some entrapped vegetable oil were dissolved at 4% by weight of pigment into isopropyl alcohol at 60° C. and the solution was allowed to cool slowly to −20° C. The pigments readily recrystallized and were again filtered using the above filter paper. These crystals were washed once with cold isopropyl alcohol to remove any remaining vegetable oil and dried.

Samples of the crude crystalline pigment and recrystallized material were analyzed in triplicate using HPLC in which pure rubropunctatin and monascorubrin were used as reference standards. The oil extracted crystals contained 44.5% by weight pigment with the remainder being virtually only adhering oil phase. The recrystallized material was 100% pigment by weight. These results indicate that after only one recrystallization the precursor pigments are pure within the accuracy of the analytical method.

Since the crude crystalline pigment contains largely adhering oil as the sole impurity, rather pure pigment may be obtained simply by washing the crude material with a solvent in which the oil is freely soluble and in which the pigment is insoluble, i.e., by washing according to methods and principles too well known to one skilled in the art to require elaboration.

What is claimed is:

1. A method of isolating crystalline water-insoluble orange pigments produced by a Monascus species in an aqueous nutrient medium containing assimilable sources of carbon, nitrogen, and inorganic substances comprising contacting the nutrient medium containing the crystalline water-insoluble pigments with a liquid vegetable oil, a mineral oil, or any mixture thereof, the contacting being for a time sufficient to effect the transfer of crystalline pigments from the aqueous nutrient medium to the oil phase, separating the oil phase, and recovering from the oil phase the insoluble crystalline pigments transferred from the aqueous nutrient medium.

2. The method of claim 1 where the oil phase is present in an amount from about 0.5 to about 20 weight percent relative to the culture medium.

3. The method of claim 2 where the oil phase is present in an amount from about 1 to about 10 weight percent.

4. The method of claim 1 where the oil phase comprises a liquid vegetable oil.

5. The method of claim 4 where the vegetable oil is selected from the group consisting of corn oil, cottonseed oil, soybean oil, safflower oil, sunflower oil, peanut oil, sesame oil, rapeseed oil, and olive oil.

6. The method of claim 1 where the oil phase comprises mineral oil.

7. The method of claim 1 where the oil phase comprises a mixture of vegetable and mineral oils.

8. A process for producing crystalline water-insoluble orange pigments from Monascus species comprising growing a Monascus species in an aqueous nutrient medium containing assimilable sources of carbon, nitrogen, and inorganic substances and a crystalline pigment inducer in an amount effective to induce crystalline pigment formation, contacting the nutrient medium containing the crystalline water-insoluble pigments with a liquid vegetable oil, a mineral oil, or any mixture thereof, for a time sufficient to effect the transfer of crystalline pigment from the aqueous nutrient medium to the oil phase, collecting the oil phase containing the crystalline pigments, collecting the nutrient medium containing the Monascus species cells and replacing depleted nutrients to afford a replenished nutrient medium with the Monascus species cells, and growing the Monascus species in said replenished nutrient medium.

9. The method of claim 8 where the oil phase comprises a liquid vegetable oil.

10. The method of claim 9 where the vegetable oil is selected from the group consisting of corn oil, cottonseed oil, soybean oil, safflower oil, sunflower oil, peanut oil, sesame oil, rapeseed oil, and olive oil.

11. The method of claim 8 where the oil phase comprises mineral oil.

12. The method of claim 8 where the oil phase comprises a mixture of vegetable and mineral oils.

13. A process for producing crystalline water-insoluble orange pigment from a Monascus species comprising in a first vessel growing Monascus species in an aqueous nutrient medium, containing assimilable sources of carbon, nitrogen, and inorganic substances and a crystalline pigment inducer in an amount effective to induce crystalline pigment formation, contacting at least a portion of the nutrient medium containing the crystalline water-insoluble pigment with a liquid vegetable oil, a mineral oil, or any mixture thereof in a second vessel for a time sufficient to effect the transfer of crystalline pigment from the nutrient medium to the oil phase, returning the nutrient medium depleted of crystalline pigment from the second vessel to the first vessel, replacing depleted nutrients in the nutrient medium of the first vessel, and periodically collecting the crystalline pigment from the oil phase.

14. The method of claim 13 where the oil phase comprises a liquid vegetable oil.

15. The method of claim 14 where the vegetable oil is selected from the group consisting of corn oil, cottonseed oil, soybean oil, safflower oil, sunflower oil, peanut oil, sesame oil, rapeseed oil, and olive oils.

16. The method of claim 13 where the oil phase comprises mineral oil.

17. The method of claim 13 where the oil phase comprises a mixture of vegetable and mineral oils.

* * * * *